(12) United States Patent
Doherty et al.

(10) Patent No.: US 9,957,438 B2
(45) Date of Patent: May 1, 2018

(54) COMPOSITIONS FOR, SOLUTIONS FOR, AND METHODS OF USE OF SILOXANE BASED AROMATIC TRISUREAS AS VISCOSIFIERS

(71) Applicants: GENERAL ELECTRIC COMPANY, Schenectady, NY (US); University of Pittsburgh—Of The Commonwealth System of Higher Education, Pittsburgh, PA (US)

(72) Inventors: Mark Daniel Doherty, Watervliet, NY (US); Michael Joseph O'Brien, Halfmoon, NY (US); Jason Lee, Pittsburgh, PA (US); Robert James Perry, Niskayuna, NY (US); Robert Enick, Bethel Park, PA (US)

(73) Assignee: General Electric Company, Schenectady, NY (US)

( * ) Notice: Subject to any disclaimer, the term of this patent is extended or adjusted under 35 U.S.C. 154(b) by 198 days.

(21) Appl. No.: 15/006,201

(22) Filed: Jan. 26, 2016

(65) Prior Publication Data
US 2017/0210975 A1    Jul. 27, 2017

(51) Int. Cl.
| | |
|---|---|
| *C09K 8/22* | (2006.01) |
| *C09K 8/32* | (2006.01) |
| *C09K 8/60* | (2006.01) |
| *C09K 8/524* | (2006.01) |
| *C09K 8/528* | (2006.01) |
| *C09K 8/54* | (2006.01) |
| *C09K 8/64* | (2006.01) |
| *C07F 7/08* | (2006.01) |
| *C07F 7/21* | (2006.01) |
| *C09K 8/82* | (2006.01) |

(52) U.S. Cl.
CPC .............. *C09K 8/64* (2013.01); *C07F 7/0854* (2013.01); *C07F 7/21* (2013.01); *C09K 8/82* (2013.01)

(58) Field of Classification Search
CPC .................. C09K 8/64; C09K 8/86
USPC ....... 507/127, 129, 137, 233, 234, 236, 239, 507/251, 263, 268
See application file for complete search history.

(56) References Cited

U.S. PATENT DOCUMENTS

| | | | |
|---|---|---|---|
| 4,913,235 A | 4/1990 | Harris et al. | |
| 5,123,486 A | 6/1992 | Davis | |
| 5,143,632 A | 9/1992 | Woo | |
| 6,191,215 B1 | 2/2001 | Beckham et al. | |
| 7,645,805 B2 | 1/2010 | Van Bommel et al. | |
| 8,828,173 B2 | 9/2014 | Weiss et al. | |
| 2011/0198534 A1* | 8/2011 | Yamanaka | C07C 275/36 252/182.12 |
| 2014/0216655 A1* | 8/2014 | Kramer | C07F 7/1836 156/330 |

FOREIGN PATENT DOCUMENTS

WO    2000035998 A2    6/2000

OTHER PUBLICATIONS

Cummings et al., "CO2: a wild solvent, tamed", Physical Chemistry Chemical Physics, 13, Issue 4, pp. 1276-1289, 2011.
Lee et al., "Development of Small Molecule CO2 Thickeners for EOR and Fracturing", SPE Improved Oil Recovery Symposium, Apr. 12-16, pp. 18, 2014, Tulsa, Oklahoma, USA.

* cited by examiner

*Primary Examiner* — Aiqun Li
(74) *Attorney, Agent, or Firm* — GE Global Patent Operation

(57) ABSTRACT

A compound represented by the following formula is provided:

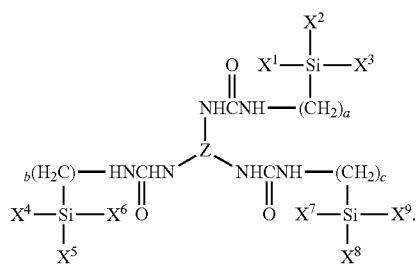

Also provided is a solution including a compound disclosed herein, a volume of dense carbon dioxide ($CO_2$), and a co-solvent, where the solution has an increased viscosity greater than the viscosity of dense $CO_2$. Methods of increasing the viscosity of dense $CO_2$ and natural gas liquids (NGLs) by, for example, dissolving a compound disclosed herein to form a solution, are also provided.

20 Claims, No Drawings

COMPOSITIONS FOR, SOLUTIONS FOR, AND METHODS OF USE OF SILOXANE BASED AROMATIC TRISUREAS AS VISCOSIFIERS

STATEMENT REGARDING FEDERALLY SPONSORED RESEARCH OR DEVELOPMENT

This invention was made with U.S. Government support under grant number DE-AR0000292, awarded by the Department of Energy, Advanced Research Projects Agency Energy. The government has certain rights in the invention.

FIELD OF INVENTION

The present invention relates generally to additive compositions for changing the viscosity of liquids, solutions including the same, and methods of use of the same to increase the viscosity of dense carbon dioxide and natural gas liquids.

BACKGROUND OF THE INVENTION

Additive compositions capable of changing the viscosity of various liquids are of considerable interest for a number of commercial and industrial applications. Dense $CO_2$, such as supercritical carbon dioxide ($scCO_2$), is of particular interest as a solvent in chemical processing. $scCO_2$ is non-flammable, relatively non-toxic, and naturally abundant. Similarly, as naturally occurring elements of natural gas, natural gas liquids (NGLs) are also of interest. High pressure hydrocarbon mixtures (for example, methane, ethane, propane, butane, and pentane) are commonly injected after primary production and many years of waterflooding to enhance oil production from subterranean layers of porous sandstone or carbonate rock.

Current fracturing and oil recovery techniques employ large amounts of water and/or $scCO_2$ to extract oil from geological formations. Aqueous fracturing and extraction methods are most common and require significant treatment and/or disposal of large quantities of produced water. Fracturing and oil recovery methods based on $scCO_2$ have several advantages including higher solubility of oil in $scCO_2$, which increases extraction efficiency, as well as a substantial decrease in the amount of aqueous waste which needs to be treated. Unfortunately the low viscosity of $scCO_2$ (~20× less than water) results in fingering, where the $scCO_2$ tends to find the path of least resistance resulting in poor overall oil recovery. The low viscosity of dense $CO_2$ as a fracturing fluid results in small fractures and difficulty in the transport of proppant particles into the fractures.

While it has been recognized that a dense $CO_2$ thickener could be a desirable solution for reducing the mobility of dense $CO_2$, thickening dense $CO_2$ is a difficult task as dense $CO_2$ is a poor solvent for most organic thickener molecules. Additives, such as high molecular weight polymers and associating polymers, have been synthesized. However, such products did not achieve both solubility in dense $CO_2$, in the absence of high volume of co-solvents, and thickening of dense $CO_2$ by altering the viscosity of dense $CO_2$.

Accordingly, there is a need to develop viscosifiers of dense $CO_2$ and NGLs, which could be used to improve oil recovery performance and/or reduce the need to treat or dispose of large quantities of produced water.

BRIEF SUMMARY OF THE INVENTION

Briefly, the present invention satisfies the need for associating molecules to thicken dense $CO_2$ and natural gas liquids (NGLs).

The present invention may address one or more problems and deficiencies of the art discussed above. However, it is contemplated that the invention may prove useful in addressing other problems and deficiencies in other areas. Therefore, the claimed invention should not necessarily be construed as limited to addressing any of the particular problems or deficiencies discussed herein.

In one aspect, the present disclosure relates to a compound of the following formula:

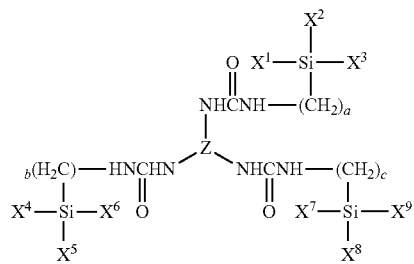

wherein Z is an aromatic moiety, a, b, and c are independently integers from 2 to 9, $X^1, X^2, X^3, X^4, X^5, X^6, X^7, X^8$, and $X^9$ are independently chosen from

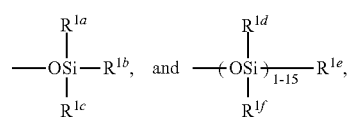

wherein $R^{1a}$, $R^{1b}$, and $R^{1c}$ are independently chosen in each instance from —$(C_{1-5})$alkyl, and

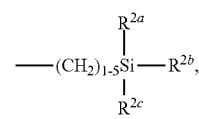

wherein $R^{2a}$, $R^{2b}$, and $R^{2c}$ are independently chosen in each instance from —$(C_{1-5})$alkyl, —$OSi((C_{1-5})$alkyl$)_3$, and —$OSi((C_{1-5})$alkyl$)_2(OSi((C_{1-5})$alkyl$)_3)$, or taken together with the Si to which they are attached, any 2 of $R^{2a}$, $R^{2b}$, and $R^{2c}$ form a fully alkylated 8 to 12 membered siloxane ring, wherein $R^{1d}$ and $R^{1f}$ are independently each —$(C_{1-5})$alkyl, and $R^{1e}$ is —$OSi((C_{1-5})$alkyl$)_2(CH_2)_{1-5}(CH_3)$, wherein when any one or more of $X^4, X^5, X^6, X^7, X^8$, and $X^9$ is each

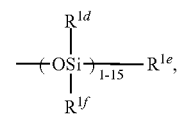

then $X^1$, $X^2$, and $X^3$ are each

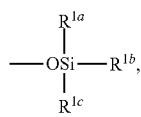

wherein $R^{1a}$, $R^{1b}$, and $R^{1c}$ are each —$(C_{1-5})$alkyl.

In another aspect, the present disclosure relates to a solution having a volume of dense $CO_2$, a compound disclosed herein, and a co-solvent, wherein the solution has a viscosity greater than the viscosity of dense $CO_2$.

In yet another aspect, the present disclosure relates to a method of increasing the viscosity of dense $CO_2$, the method includes dissolving a compound disclosed herein in a co-solvent to form a solution and mixing the solution with a volume of dense $CO_2$.

In yet another aspect, the present disclosure relates to a method of increasing the viscosity of natural gas liquids (NGLs), the method includes dissolving a compound disclosed herein in a volume of NGL.

DETAILED DESCRIPTION OF THE INVENTION

Aspects of the present invention and certain features, advantages, and details thereof, are explained more fully below with references to non-limiting embodiments of the invention.

Descriptions of well-known materials, equipment and tools, processing techniques, etc., are omitted so as to not unnecessarily obscure the invention in detail. It should be understood, however, that the detailed description and the specific examples, while indicating embodiments of the invention, are given by way of illustration only, and are not by way of limitation. Various substitutions, modifications, additions and/or arrangements within the spirit and/or scope of the underlying inventive concepts will be apparent to those skilled in the art from this disclosure, and such embodiments fall within the scope of the invention as defined by the claims that follow.

All patents, publications, applications and other references cited herein are hereby incorporated in their entirety into the present application.

In practicing the present invention, many conventional techniques in chemistry, and organic chemistry are used, which are within the skill of the ordinary artisan. The contents of references containing standard protocols, widely known to and relied upon by those of skill in the art, including manufacturers' instructions are hereby incorporated by reference as part of the present disclosure.

Unless otherwise specified, "alkyl" is intended to include linear or branched structures.

"Cycloalkyl" is a subset of alkyl and includes cyclic hydrocarbon groups of from 3 to 10 carbon atoms. Examples of cycloalkyl groups include cyclopropyl, cyclobutyl, cyclopentyl, cyclohexyl, norbornyl and the like.

"Hydrocarbon" refers to any substituent comprised of hydrogen and carbon as the only elemental constituents.

"Aromatic" or "heteroaromatic" refers to (i) a phenyl group (or benzene) or a monocyclic 5- or 6-membered ring containing 1-4 heteroatoms selected from O, N, or S; (ii) a bicyclic 9- or 10-membered aromatic or heteroaromatic ring system containing 0-4 heteroatoms selected from O, N, or S; or (iii) a tricyclic 13- or 14-membered aromatic or heteroaromatic ring system containing 0-5 heteroatoms selected from O, N, or S. The aromatic 6- to 14-membered carbocyclic rings include, e.g., benzene, naphthalene, indane, tetralin, and fluorene and the 5- to 10-membered aromatic heterocyclic rings include, e.g., imidazole, pyridine, indole, thiophene, benzopyranone, thiazole, furan, benzimidazole, quinoline, isoquinoline, quinoxaline, pyrimidine, pyrazine, tetrazole and pyrazole.

"Polycyclic aromatic" or "polycyclic heteroaromatic" is a subset of aromatic and heteroaromatic, and refers to a ring system containing 2 or more aromatic or heteroaromatic rings. Examples include, e.g., naphthalene, anthracene, phenanthrene, tetracene, triphenylene, quinoline, indole, and fluorene.

As used herein, "solvent" or "co-solvent" refers to $C_3$-$C_{16}$ hydrocarbon and may refer to a single solvent or a mixture of solvents, unless indicated otherwise. Examples include, e.g. propane, butane, pentane, hexane, heptane, methanol, ethanol, toluene, xylene, and combinations thereof.

As used herein, "dense $CO_2$" refers to a fluid state of carbon dioxide and may refer to supercritical $CO_2$ or liquid $CO_2$. In some embodiments, supercritical state of $CO_2$ may be preferable.

In one aspect, the present disclosure relates to a compound of the following formula:

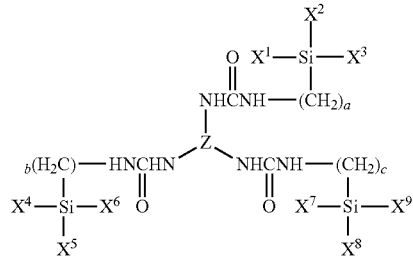

wherein Z is an aromatic moiety,
a, b, and c are independently integers from 2 to 9,
$X^1$, $X^2$, $X^3$, $X^4$, $X^5$, $X^6$, $X^7$, $X^8$, and $X^9$ are independently chosen from

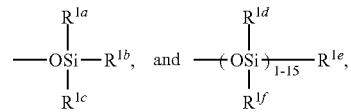

wherein $R^{1a}$, $R^{1b}$, and $R^{1c}$ are independently chosen in each instance from —$(C_{1-5})$alkyl, and

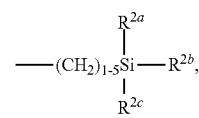

wherein $R^{2a}$, $R^{2b}$, and $R^{2c}$ are independently chosen in each instance from —$(C_{1-5})$alkyl, —$OSi((C_{1-5})$alkyl$)_3$, and —$OSi((C_{1-5})$alkyl$)_2(OSi((C_{1-5})$alkyl$)_3)$, or taken together with the Si to which they are attached, any 2 of $R^{2a}$, $R^{2b}$, and $R^{2c}$ form a fully alkylated 8 to 12 membered siloxane ring,
wherein $R^{1d}$ and $R^{1f}$ are independently each —$(C_{1-5})$alkyl, and $R^{1e}$ is $-OSi((C_{1-5})alkyl)_2(CH_2)_{1-5}(CH_3)$,
wherein when any one or more of $X^4$, $X^5$, $X^6$, $X^7$, $X^8$, and $X^9$ is each

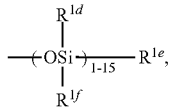

then $X^1$, $X^2$, and $X^3$ are each

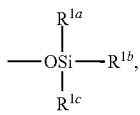

wherein $R^{1a}$, $R^{1b}$, and $R^{1c}$ are each $-(C_{1-5})alkyl$.

In certain embodiments, Z may be selected from an aromatic ring, a heteroaromatic ring, a polycyclic aromatic ring system, and a polycyclic heteroaromatic ring system. In certain embodiments, Z may be a $(C_{6-10})$ aromatic ring or polycyclic aromatic ring. In certain embodiments, the aromatic ring may be

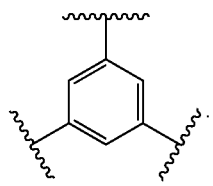 [SMILES: *c1cc(*)cc(*)c1]

In certain embodiments, $X^1$, $X^2$, $X^3$, $X^4$, $X^5$, $X^6$, $X^7$, $X^8$, and $X^9$ may each be

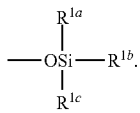

In some embodiments, $R^{1a}$, $R^{1b}$, and $R^{1c}$ may be the same. In certain embodiments, $R^{1a}$, $R^{1b}$, and $R^{1c}$ may be $-(C_1-C_5)alkyl$. In certain embodiments, for example, $R^{1a}$, $R^{1b}$, and $R^{1c}$ may be $-CH_3$. In some embodiments, any two of $R^{1a}$, $R^{1b}$, and $R^{1c}$ may be the same. In some embodiments, each of $R^{1a}$, $R^{1b}$, and $R^{1c}$ may be different.

In some embodiments, $R^{1a}$, $R^{1b}$, and $R^{1c}$ may each be

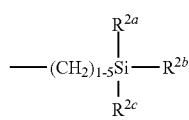

and $R^{2a}$, $R^{2b}$, and $R^{2c}$ may be independently chosen in each instance from $-(C_{1-5})alkyl$, $-OSi((C_{1-5})alkyl)_3$, and $-OSi((C_{1-5})alkyl)_2(OSi((C_{1-5})alkyl)_3)$. In some embodiments, each of $R^{2a}$, $R^{2b}$, and $R^{2c}$ may be the same. In some embodiments, any two of $R^{2a}$, $R^{2b}$, and $R^{2c}$ may be the same. In some embodiments, each of $R^{2a}$, $R^{2b}$, and $R^{2c}$ may be different.

In some embodiments, $R^{1a}$, $R^{1b}$, and $R^{1c}$ may each be

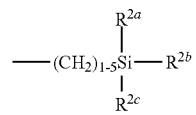

and $R^{2a}$ may be $-(C_{1-5})alkyl$ and taken together with the Si to which they are attached, $R^{2b}$ and $R^{2c}$ may form a fully alkylated 8 to 12 membered siloxane ring. A fully alkylated siloxane ring is formed when, for example, each Si is attached to a substituent that is not a hydrogen.

In some embodiments, any two of $R^{1a}$, $R^{1b}$, and $R^{1c}$ may be $-(C_1-C_5)alkyl$ and any one of $R^{1a}$, $R^{1b}$, and $R^{1c}$ may be

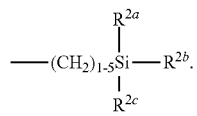

In some embodiments, any one of $R^{1a}$, $R^{1b}$, and $R^{1c}$ may be $-(C_1-C_5)alkyl$ and any two of $R^{1a}$, $R^{1b}$, and $R^{1c}$ may each be

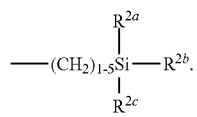

In some embodiments, for example, $X^1$, $X^2$, and $X^3$, may each be

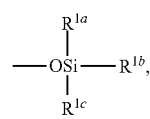

wherein $R^{1a}$, $R^{1b}$, and $R^{1c}$ may be $-CH_3$, and $X^4$, $X^5$, $X^6$, $X^7$, $X^8$, and $X^9$ may each be

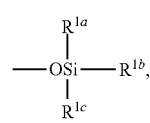

wherein $R^{1a}$, $R^{1b}$, and $R^{1c}$ may each be

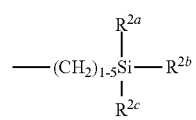

and $R^{2a}$ may be $-CH_3$ and taken together with the Si to which they are attached, $R^{2b}$ and $R^{2c}$ may form a fully alkylated 8 to 12 membered siloxane ring.

In some embodiments, for example, $X^1$, $X^2$, $X^3$, $X^4$, $X^5$, and $X^6$, may each be

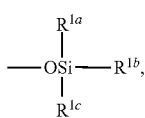

wherein $R^{1a}$, $R^{1b}$, and $R^{1c}$ may be —$CH_3$, and $X^7$, $X^8$, and $X^9$ may each be

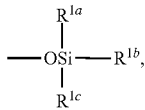

wherein $R^{1a}$, $R^{1b}$, and $R^{1c}$ may each be

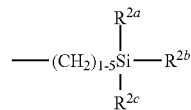

and $R^{2a}$ may be —$CH_3$ and taken together with the Si to which they are attached, $R^{2b}$ and $R^{2c}$ may form a fully alkylated 8 to 12 membered siloxane ring.

In some embodiments, for example, $X^1$, $X^2$, and $X^3$, may each be

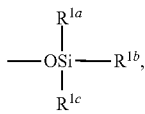

wherein $R^{1a}$, $R^{1b}$, and $R^{1c}$ may be —$CH_3$; and $X^4$, $X^5$, $X^6$, $X^7$, $X^8$, and $X^9$ may each be

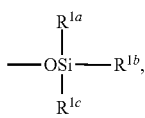

wherein $R^{1a}$, and $R^{1c}$ may be —$CH_3$, and wherein $R^{1b}$ may be

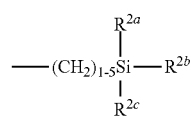

wherein $R^{2a}$, $R^{2b}$ and $R^{2c}$ may each be —$OSi(CH_3)_3$.

In some embodiments, for example, $X^1$, $X^2$, $X^3$, $X^4$, $X^5$, and $X^6$, may each be

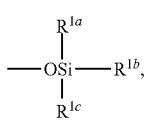

wherein $R^{1a}$, $R^{1b}$, and $R^{1c}$ may each be —$CH_3$; and $X^7$, $X^8$, and $X^9$ may each be

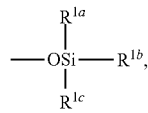

wherein $R^{1a}$, and $R^{1c}$ may each be —$CH_3$, and wherein $R^{1b}$ may be

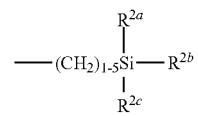

wherein $R^{2a}$, $R^{2b}$ and $R^{2c}$ may each be —$OSi(CH_3)_3$.

In some embodiments, two or less of $X^1$, $X^2$, $X^3$, $X^4$, $X^5$, $X^6$, $X^7$, $X^8$, and $X^9$ may each be

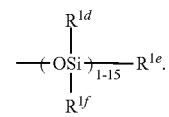

In some embodiments, any two of $X^4$, $X^5$, $X^6$, $X^7$, $X^8$, and $X^9$ may each be

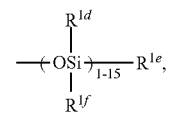

and $X^1$, $X^2$, and $X^3$ may each be

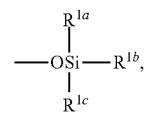

wherein $R^{1a}$, $R^{1b}$, and $R^{1c}$ are each —$(C_{1-5})$alkyl. For example, in certain embodiments, $X^1$, $X^2$, and $X^3$ may each be —$(OSi(CH_3)_3)_3$, and $X^4$, $X^6$, $X^7$, and $X^9$ may each be —$CH_3$, and $X^5$, and $X^8$, may each be —$(OSi(CH_3)_2)_{11}(CH_2)_3 CH_3)$.

In some embodiments, any one of $X^1$, $X^2$, $X^3$, $X^4$, $X^5$, $X^6$, $X^7$, $X^8$ and $X^9$ may be

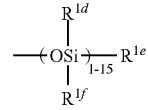

and $X^1$, $X^2$, and $X^3$ may each be

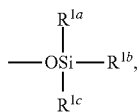

wherein $R^{1a}$, $R^{1b}$, and $R^{1c}$ are each —$(C_{1-5})$alkyl. In certain embodiments, for example, $X^1$, $X^2$, $X^3$, $X^4$, $X^5$, and $X^6$ may each be —$(OSi((CH_3)_3)_3)$; $X^7$ and $X^9$ may each be —$CH_3$; and $X^8$, and may be —$(OSi(CH_3)_2)_{11}(CH_2)_3CH_3)$.

In a certain embodiment, Z may be

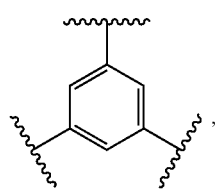 [SMILES: *c1cc(*)cc(*)c1]

a, b, and c may each be 3, and $X^1$, $X^2$, $X^3$, $X^4$, $X^5$, $X^6$, $X^7$, $X^8$, and $X^9$ may each be

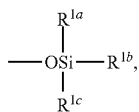

wherein $R^{1a}$, $R^{1b}$ and $R^{1c}$ may be —$CH_3$.

In a certain embodiment, Z may be

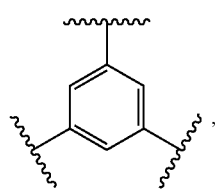

a, b, and c may each be 3, and $X^1$, $X^2$, $X^3$, $X^4$, $X^5$, $X^6$, $X^7$, $X^8$, and $X^9$ may each be

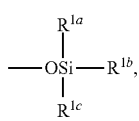

wherein $R^{1a}$ and $R^{1c}$ may each be —$CH_3$, and $R^{1b}$ may be

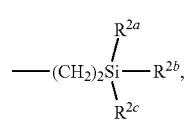

and wherein $R^{2a}$, $R^{2b}$, and $R^{2c}$ taken together with the Si to which they are attached may form

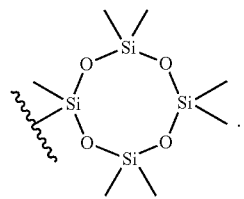

In another embodiment, Z may be

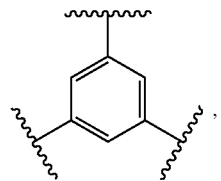 [SMILES: *c1cc(*)cc(*)c1]

a, b, and c may each be 3, and $X^1$, $X^2$, $X^3$, $X^4$, $X^5$, and $X^6$ may each be

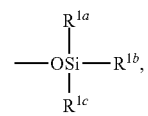

wherein $R^{1a}$, $R^{1b}$, and $R^{1c}$ may be —$CH_3$, $X^7$ and $X^9$ may each be —$CH_3$, and $X^8$ may be

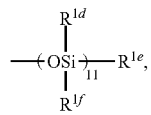

wherein $R^{1d}$ and $R^{1f}$ may be —$CH_3$, and $R^{1e}$ may be —$OSi(CH_3)_2(CH_2)_3(CH_3)$.

In another aspect, the present disclosure relates to a solution having a volume of dense $CO_2$, a compound disclosed herein, and a co-solvent, wherein the solution has a viscosity greater than the viscosity of dense $CO_2$. For example, the viscosity of the solution is greater as compared to the viscosity of dense $CO_2$. In some embodiments, the co-solvent is a $C_3$-$C_{16}$ hydrocarbon solvent. Examples of $C_3$-$C_{16}$ hydrocarbon solvent include propane, butane, pentane, hexane, heptane, methanol, ethanol, toluene, and xylene.

In another aspect, the present disclosure relates to a method of increasing viscosity of dense $CO_2$, the method includes: dissolving a compound disclosed herein in a co-solvent to form a solution; and mixing the solution with a volume of dense $CO_2$. In some embodiments, the compound being dissolved may be an amount between 0.01 and 5 wt. %, preferably between 0.1 and 1 wt. %, based on the weight of the resultant mixed solution. For example, the compound being dissolved may be an amount between 0.4 to 0.6 wt. %. In certain embodiments, the compound being dissolved may be 0.5 wt. %. In certain other embodiments, the compound being dissolved may be 1 wt. %. In certain other embodiments, the compound being dissolved may be 1.5 wt. %.

In some embodiments, the co-solvent used to dissolve the compound may be an amount between 1 and 50 wt. % based on the weight of the resultant mixed solution. In certain embodiments, the mixing of the solution with a volume of dense $CO_2$ may be performed at a temperature between 20° C. and 100° C., and under pressure within the range of 800 psi and 9000 psi.

In another aspect, the present disclosure relates to a method of increasing viscosity of natural gas liquids (NGLs), the method includes: dissolving a compound disclosed herein in a volume of an NGL to form a solution. In some embodiments, the NGL includes one or more gas liquids selected from a group that includes propane, butane, iso-butane, pentane, and pentane plus.

In some embodiments, the compound being dissolved may be an amount between 0.01 and 5 wt. %, preferably between 0.1 and 1 wt. %, based on the weight of the resultant solution. In certain embodiments, the dissolving of the compound with a volume of NGL may be performed at a temperature between 20° C. and 120° C., and under pressure within the range of 50 psi and 10,000 psi.

EXAMPLES

In general, the compounds of the present invention may be prepared by the methods illustrated in the general reaction schemes as, for example, described below, or by modifications thereof, using readily available starting materials, reagents and conventional synthesis procedures. In these reactions, it is also possible to make use of variants that are in themselves known, but are not mentioned here.

Compound A. Benzene-1,3,5-tris(tris(trimethylsiloxy)silylpropylurea)

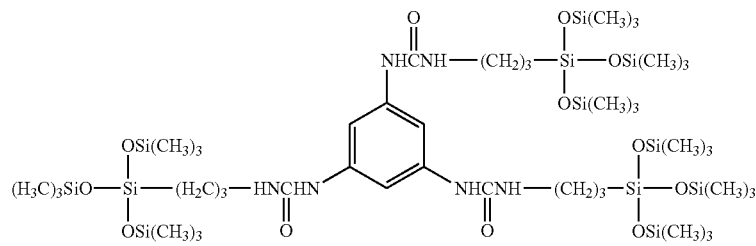

Sodium azide (1.75 g, 26.919 mmol, 7 equiv.) was dissolved in 10 mL of deionized water and cooled to 0° C. Separately, 1,3,5-benzenetricarbonyl chloride (1.006 g, 3.789 mmol, 1 equiv.) was dissolved in 10 mL of tetrahydrofuran (THF) and cooled to 0° C. The acid chloride solution was added to the stirring sodium azide solution resulting in the formation of 1,3,5-benzenetricarbonyl azide as a white precipitate. The mixture was stirred at 0° C. for 2 hours behind a blast shield at which point 200 mL of cold toluene and 10 mL of water were added to dissolve all solids. The toluene layer was isolated, washed with water (3×80 mL), saturated aqueous brine (80 mL), dried over magnesium sulfate ($MgSO_4$) and filtered. The filtrate was collected and transferred to a round bottom flask fitted with a reflux condenser connected to a nitrogen inlet and heated to 100° C. for several hours until gas evolution ($N_2$ extrusion) ceased. The solution was then removed from the oil bath and aminopropyltris(trimethylsiloxy)silane (4.022 g, 11.369 mmol, 3.00 equiv.) was added to the hot toluene solution and stirred vigorously overnight. As the mixture cooled to room temperature, it became hazy and the viscosity of the solution increased. The volatiles were then removed under vacuum to produce the intended product as a pale yellow solid (3.291 g, 2.607 mmol, 69% yield). $^1$H NMR ($CDCl_3$, 400.13 MHz) δ (ppm): 8.24 (broad s, 0.5H, NH), 8.72 (broad s, 3.4H, $H_{Ar}$), 5.38 (broad s, 0.6H, NH), 3.15 (broad s, 4.9H, $NHCH_2$), 1.55 (broad s, 9.0H, $CH_2CH_2Si$), 0.46 (broad s, 6.0H, $CH_2Si$), 0.30 to −0.15 (84.0H, SiMe). $^{13}$C NMR ($CDCl_3$, 100.62 MHz) δ (ppm): 43.20, 24.25, 11.95, 1.85, 1.74.

Solubility in $CO_2$ and thickening efficacy of Compound A was assessed and the results are shown in Tables 1 and 2 below. As used herein, the term "cloud point" refers to the pressure at which the material begins to precipitate from an optically transparent solution in dense $CO_2$ at a given temperature to form a cloudy, optically opaque mixture.

TABLE 1

Cloud Point for Compound A.

| Amount of Compound | Co-Solvent | $CO_2$ | Pressure/Temperature |
|---|---|---|---|
| 1.6 wt. % | 48.4 wt. % hexanes | 50 wt. % | 1280 psi @ 25° C.; 2200 psi @ 70° C. |
| 1.3 wt. % | 38.7 wt. % hexanes | 60 wt. % | 8800 psi @ 25° C.; 6100 psi @ 74° C. |
| 0.5 wt. % | 39.5 wt. % hexanes | 60 wt. % | >800 psi |
| 0.1 wt. % | 25 wt. % hexanes | 74.9 wt. % | Insoluble up to 80° C. |
| 0.1 wt. % | — | 99.9 wt. % | Insoluble |

TABLE 2

Viscosity Effects of Compound A.

| Viscosity | Amount of Compound | Co-Solvent | $CO_2$ | Pressure/Temperature |
|---|---|---|---|---|
| 320X increase | 1.6 wt. % | 48.4 wt. % hexanes | 50 wt. % | 25° C. |
| 100X increase | 1.3 wt. % | 38.7 wt. % hexanes | 60 wt. % | 25° C. |
| 14.4X increase | 0.5 wt. % | 39.5 wt. % hexanes | 60 wt. % | 25° C. and 8000 psi |
| 12.8X increase | 0.5 wt. % | 39.5 wt. % hexanes | 60 wt. % | 25° C. and 6000 psi |

Compound A is also soluble in NGLs and increases the viscosity of NGLs. For example, the cloud point for 1.5 wt. % of Compound A in 98.5 wt. % butane was at 192 psi at 80° C., with 2× increase in viscosity; at 154 psi at 60°, with 10× increase; at 124 psi at 40° C., with 50× increase; and at 65 psi at 25° C., with 300× increase in viscosity.

Compound B. Hyperbranched Benzene Trisurea

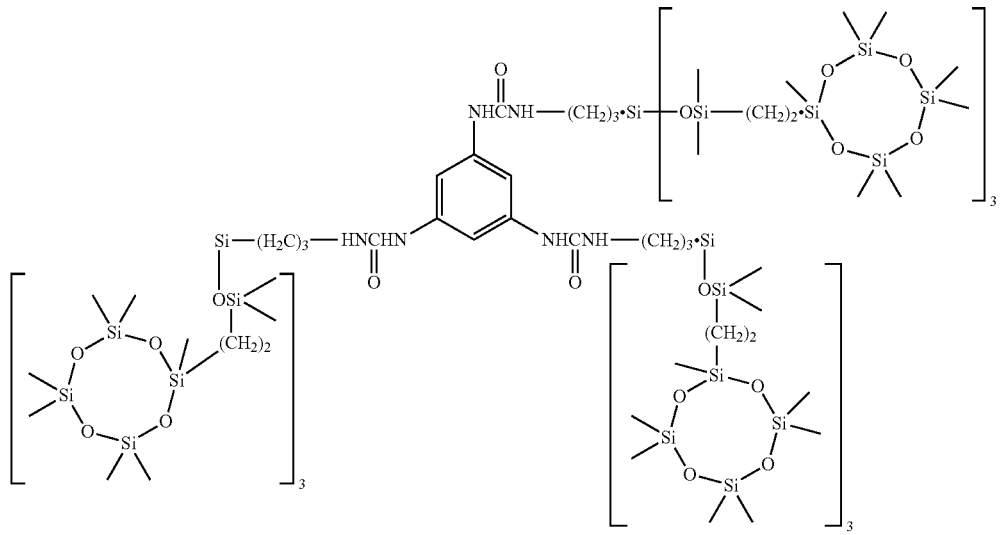

Compound B, a hyberbranched benzene trisurea, was prepared according the procedure described for Compound A using sodium azide (0.50433 g, 7.758 mmol, 7.2 equiv.) dissolved in 10 mL of deionized water and cooled to 0° C. Separately, 1,3,5-benzenetricarbonyl chloride (0.28609 g, 1.081 mmol, 1 equiv.) was dissolved in 10 mL of THF and cooled to 0° C. and cyclic siloxane functionalized aminopropyl siloxane, $H_2N(CH_2)_3Si\{OSi(CH_3)_2CH_2CH_2[(CH_3)Si(cyclo-(OSi(CH_3)_2)_3)]\}_3$, (4.00051 g, 3.232 mmol, 3.0 equiv.) was dissolved in 10 mL of toluene. The product was isolated as a pale yellow liquid (1.6687 g, 0.4264 mmol, 40% yield). $^1$H NMR (CDCl$_3$, 400.13 MHz) δ (ppm): 7.21 (broad s, 2.3H, H$_{Ar}$), 6.32 (broad s, 3.4H, NH), 4.60 (broad s, 2.1H, NH), 3.21 (broad q, 6.0H, J=7.0 Hz, NCH$_2$), 1.56 (broad mult, 8.3H, NCH$_2$CH$_2$), 0.60 to 0.40 (overlapping broad mult, 50.2H, 21×SiCH$_2$), 0.30 to −0.10 (302.9H, SiMe). 13C NMR (CDCl3, 150.72 MHz) δ (ppm): 155.85, 139.93, 130.26, 128.42, 128.00, 125.42, 106.03, 64.52, 43.18, 34.15, 30.28, 24.98, 24.14, 11.83, 9.18, 8.46, 1.80, 0.76, 0.68, −0.58, −1.59.

The cloud point for 1 wt. % of Compound B was at 3000 psi at 25° C., with a 15% increase in viscosity.

Compound C. Mixed Benzene Trisurea

Compound C, a mixed benzene trisurea, was prepared according to the procedure described for Compound A using sodium azide (1.763 g, 27.119 mmol, 7.2 equiv.) dissolved in 10 mL of deionized water and cooled to 0° C., 1,3,5-benzenetricarbonyl chloride (1.0031 g, 3.778 mmol, 1 equiv.) dissolved in 10 mL of THF and cooled to 0° C. and a mixture containing a 2:1 molar ratio of aminopropyltris(trimethylsiloxy)silane (2.665 g, 7.532 mmol, 1.99 equiv.) to $H_2N(CH_2)_3Si(CH_3)2(OSi(CH_3)_2)_{11}Si(CH_3)_2(CH_2CH_2\ CH_2\ CH_3)$ (3.975 g, 3.792 mmol, 1.00 equiv.). The product was isolated as a waxy white solid (6.385 g, 3.262 mmol, 87% yield). $^1$H NMR (CD3OD, 400.13 MHz) δ (ppm): 7.12 (s, 2.8H, H$_{Ar}$), 3.17 (broad t, 6.0H, J=7.0 Hz, NCH$_2$), 1.58 (broad mult, 6.4H, NCH$_2$CH$_2$), 1.37 (broad mult, 4.8H, SiCH$_2$CH$_2$CH$_2$CH$_3$), 0.93 (broad t, 3.0H, J=6.3 Hz, SiCH$_2$CH$_2$CH$_2$CH$_3$), 0.70 to 0.45 (overlapping broad mult, 8.2H, SiCH$_2$), 0.35 to −0.30 (130.6H, SiMe). $^{13}$C NMR (CD$_3$OD, 150.72 MHz) δ (ppm): 156.79, 140.35, 103.85, 42.42, 42.12, 26.07, 25.28, 24.03, 23.81, 17.55, 14.89, 12.83, 11.27, 0.51, 0.07, −0.97.

Where certain moieties are added in molar ratios, then the resultant may be a mixture having a statistical distribution of several compounds. For example, in preparing Compound C, the siloxane containing moiety is added in a 2:1 molar ratio. The resulting compounds may include, for example, compounds wherein 2 of the ureas are attached to branched siloxane and 1 of the ureas is attached to a linear siloxane, compounds where only 1 of the ureas is attached to a branched siloxane, etc.

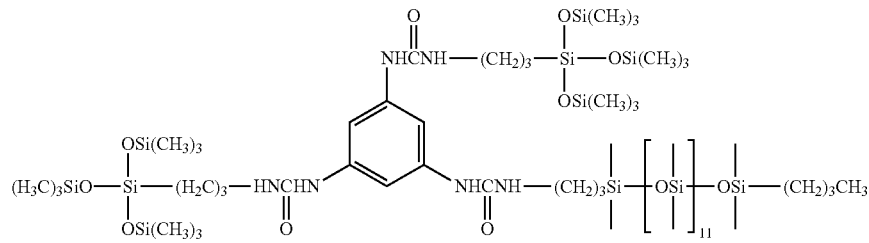

The cloud point for 1.5 wt. % of Compound C with 18.5 wt. % hexanes and 80 wt. % $CO_2$ was 4670 psi @ 25° C., with 30× increase in viscosity. 1 wt. % of Compound C with 19 wt. % hexanes and 80 wt. % $CO_2$ provided a 5× increase in viscosity.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprise" (and any form of comprise, such as "comprises" and "comprising"), "have" (and any form of have, such as "has" and "having"), "include" (and any form of include, such as "includes" and "including"), "contain" (and any form contain, such as "contains" and "containing"), and any other grammatical variant thereof, are open-ended linking verbs. As a result, a method or device that "comprises", "has", "includes" or "contains" one or more steps or elements possesses those one or more steps or elements, but is not limited to possessing only those one or more steps or elements. Likewise, a step of a method or an element of a device that "comprises", "has", "includes" or "contains" one or more features possesses those one or more features, but is not limited to possessing only those one or more features.

As used herein, the terms "comprising," "has," "including," "containing," and other grammatical variants thereof encompass the terms "consisting of" and "consisting essentially of."

Subject matter incorporated by reference is not considered to be an alternative to any claim limitations, unless otherwise explicitly indicated.

Where one or more ranges are referred to throughout this specification, each range is intended to be a shorthand format for presenting information, where the range is understood to encompass each discrete point within the range as if the same were fully set forth herein. Any numerical values recited herein include all values from the lower value to the upper value in increments of one unit provided that there is a separation of at least 2 units between any lower value and any higher value. For values which are less than one, one unit is considered to be 0.0001, 0.001, 0.01 or 0.1 as appropriate. As an example, if it is stated that the amount of a component is, for example, between 0.01 and 5 wt. %, preferably between 0.1 and 1 wt. %, etc., it is intended that values such as 0.02 to 0.8 wt. %, 0.4 to 0.6 wt. %, 4.1 to 4.8 wt. %, etc. are expressly enumerated in this specification. These are only examples of what is specifically intended and all possible combinations of numerical values between the lowest value and the highest value enumerated are to be considered to be expressly stated in this application in a similar manner.

While several aspects and embodiments of the present invention have been described and depicted herein, alternative aspects and embodiments may be affected by those skilled in the art to accomplish the same objectives. Accordingly, this disclosure and the appended claims are intended to cover all such further and alternative aspects and embodiments as fall within the true spirit and scope of the invention.

What is claimed is:

1. A compound of the following formula:

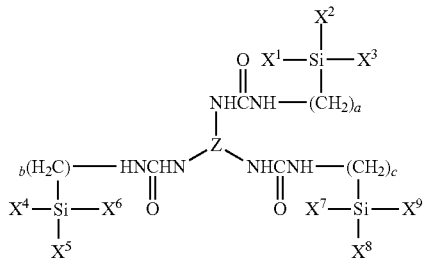

wherein Z is an aromatic moiety,
a, b, and c are independently integers from 2 to 9,
$X^1$, $X^2$, $X^3$, $X^4$, $X^5$, $X^6$, $X^7$, $X^8$, and $X^9$ are independently chosen from

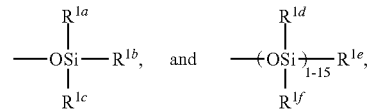

wherein $R^{1a}$, $R^{1b}$, and $R^{1c}$ are independently chosen in each instance from —$(C_{1-5})$alkyl, and

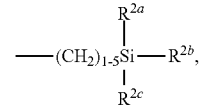

wherein $R^{2a}$, $R^{2b}$, and $R^{2c}$ are independently chosen in each instance from —$(C_{1-5})$alkyl, —OSi$((C_{1-5})$alkyl$)_3$, and —OSi$((C_{1-5})$alkyl$)_2$(OSi$((C_{1-5})$alkyl$)_3$), or taken together with the Si to which they are attached, any 2 of $R^{2a}$, $R^{2b}$, and $R^{2c}$ form a fully alkylated 8 to 12 membered siloxane ring,
wherein $R^{1d}$ and $R^{1f}$ are independently each —$(C_{1-5})$alkyl, and
$R^{1e}$ is —OSi$((C_{1-5})$alkyl$)_2$$(CH_2)_{1-5}$$(CH_3)$,
wherein when any one or more of $X^4$, $X^5$, $X^6$, $X^7$, $X^8$, and $X^9$ is each

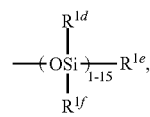

then $X^1$, $X^2$, and $X^3$ are each

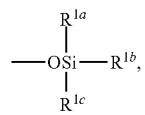

wherein $R^{1a}$, $R^{1b}$, and $R^{1c}$ are each —$(C_{1-5})$alkyl.

2. The compound of claim 1, wherein Z is selected from an aromatic ring, a heteroaromatic ring, a polycyclic aromatic ring system, or a polycyclic heteroaromatic ring system.

3. The compound of claim 1, wherein Z is a ($C_{6-10}$) aromatic ring or a polycyclic aromatic ring.

4. The compound of claim 1, wherein $X^1$, $X^2$, $X^3$, $X^4$, $X^5$, $X^6$, $X^7$, $X^8$, and $X^9$ are each

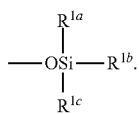

5. The compound of claim 1, wherein two or less of $X^1$, $X^2$, $X^3$, $X^4$, $X^5$, $X^6$, $X^7$, $X^8$, and $X^9$ are each

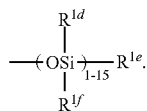

6. The compound of claim 1, wherein Z is

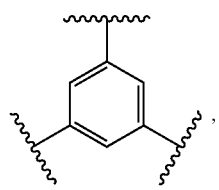 [SMILES: *c1cc(*)cc(*)c1]

a, b, and c are each 3, and
$X^1$, $X^2$, $X^3$, $X^4$, $X^5$, $X^6$, $X^7$, $X^8$, and $X^9$ are each

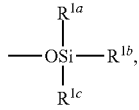

wherein $R^{1a}$, $R^{1b}$, and $R^{1c}$ are each —$CH_3$.

7. The compound of claim 1, wherein Z is

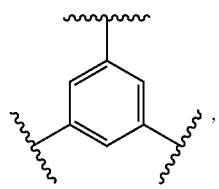 [SMILES: *c1cc(*)cc(*)c1]

a, b, and c are each 3, and
$X^1$, $X^2$, $X^3$, $X^4$, $X^5$, $X^6$, $X^7$, $X^8$, and $X^9$ are each

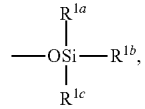

wherein $R^{1a}$, and $R^{1c}$ are each —$CH_3$ and $R^{1b}$ is

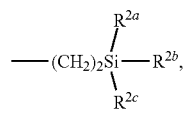

and wherein $R^{2a}$, $R^{2b}$, and $R^{2c}$ taken together with the Si to which they are attached form

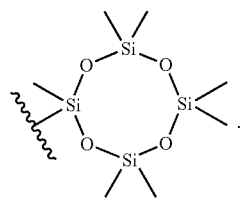

8. The compound of claim 1, wherein Z is

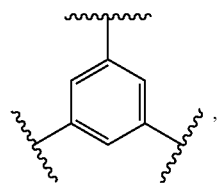 [SMILES: *c1cc(*)cc(*)c1]

a, b, and c are each 3,
$X^1$, $X^2$, $X^3$, $X^4$, $X^5$, and $X^6$ are each

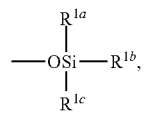

wherein $R^{1a}$, $R^{1b}$, and $R^{1c}$ are —$CH_3$,
$X^7$ and $X^9$ are each —$CH_3$, and
$X^8$ is

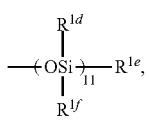

wherein $R^{1d}$ and $R^{1f}$ are —$CH_3$, and $R^{1e}$ is —$OSi(CH_3)_2(CH_2)_3(CH_3)$.

9. A solution comprising a volume of dense $CO_2$, a compound of claim 1, and a co-solvent, wherein the solution has a viscosity greater than the viscosity of dense $CO_2$.

10. The solution of claim 9, wherein the co-solvent is a $C_3$-$C_{16}$ hydrocarbon solvent.

11. A method of increasing viscosity of dense $CO_2$ comprising:
dissolving a compound in accordance with claim 1 in a co-solvent to form a solution; and
mixing the solution with a volume of dense $CO_2$.

12. The method of claim 11, wherein the compound is an amount between 0.01 and 5 wt. % based on the weight of the resultant mixed solution.

13. The method of claim 12, wherein the compound is an amount between 0.1 and 1 wt. % based on the weight of the resultant mixed solution.

14. The method of claim 11, wherein the co-solvent used to dissolve the compound is an amount between 1 and 50 wt. % based on the weight of the resultant mixed solution.

15. The method of claim 11, wherein the mixing of the solution with a volume of dense $CO_2$ is performed at a temperature between 20° C. and 100° C., and under pressure within the range of 800 psi and 9000 psi.

16. A method of increasing viscosity of natural gas liquids (NGLs) comprising:
dissolving a compound in accordance with claim 1 in a volume of an NGL to form a solution.

17. The method of claim 16, wherein the NGL comprises one or more gases selected from a group consisting of propane, butane, iso-butane, pentane, and pentane plus.

18. The method of claim 16, wherein the compound is an amount between 0.01 and 5 wt. % based on the weight of the resultant solution.

19. The method of claim 16, wherein the compound is an amount between 0.1 and 1 wt. % based on the weight of the resultant solution.

20. The method of 16, wherein the dissolving of the compound with a volume of NGL is performed at a temperature between 20° C. and 120° C., and under pressure within the range of 50 psi and 10,000 psi.

* * * * *